United States Patent [19]

Niskin

[11] 4,091,676
[45] May 30, 1978

[54] WATER SAMPLE COLLECTING DEVICE

[76] Inventor: Shale J. Niskin, 2941 Lucaya, Coconut Grove, Fla. 33133

[21] Appl. No.: 788,588

[22] Filed: Apr. 18, 1977

Related U.S. Application Data

[63] Continuation-in-part of Ser. No. 691,905, June 1, 1976, Pat. No. 4,037,477.

[51] Int. Cl.² ............ F16J 15/32; G01N 1/10
[52] U.S. Cl. .................. 73/425.4 R; 73/300; 277/30
[58] Field of Search .......... 73/425.4 R, 300, 422 TC, 73/425.4; 33/126.4 R, 126.4 A; 251/315; 277/30, 100

[56] References Cited

U.S. PATENT DOCUMENTS

| | | | |
|---|---|---|---|
| 1,838,729 | 12/1931 | Andrews | 73/425.4 R |
| 2,314,372 | 3/1943 | Spilhaus | 73/425.4 R |
| 2,391,978 | 1/1946 | Kahl | 73/425.4 R |
| 3,161,053 | 12/1964 | Bell | 73/425.4 R |
| 3,563,265 | 2/1971 | Graham | 251/315 X |
| 3,576,309 | 4/1971 | Zawacke | 251/315 X |
| 3,841,156 | 10/1974 | Wolfe | 73/425.4 R X |
| 4,037,477 | 7/1977 | Niskin | 73/425.4 R |

FOREIGN PATENT DOCUMENTS 12,119 of 1907 United Kingdom .......... 33/126.4 R Primary Examiner—Daniel M. Yasich

[57] ABSTRACT

A water sample collecting device for obtaining a sample of water at a predetermined depth consisting of a tubular member with spherical valves at both ends and means for maintaining the valves in a closed position when launched, opening the valves after the device is descending in the water to permit flushing of the device until the device has reached the desired depth when a messenger causes the valves to rotate to the closed position at which time the device containing the sample of water is brought to the surface.

7 Claims, 27 Drawing Figures

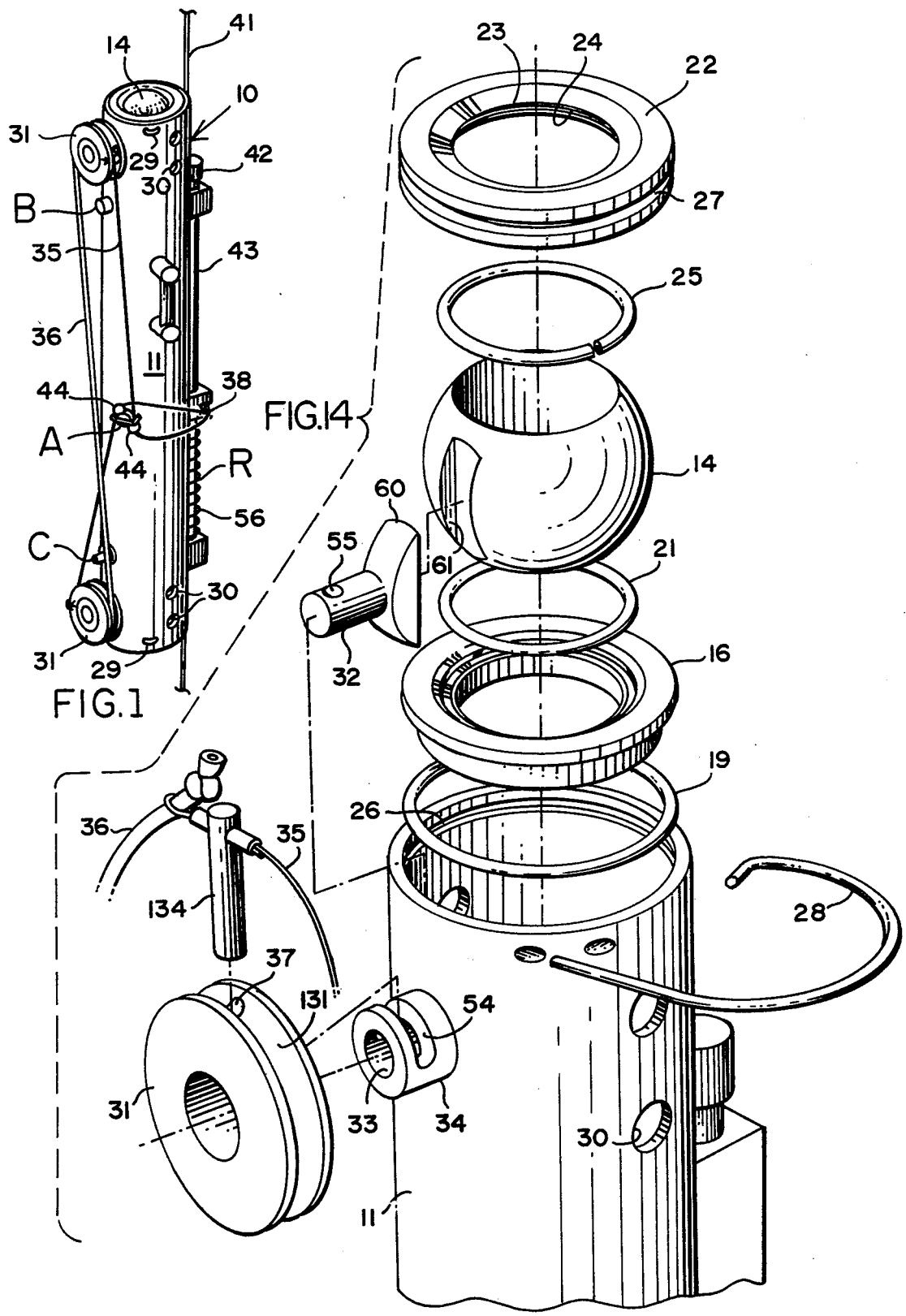

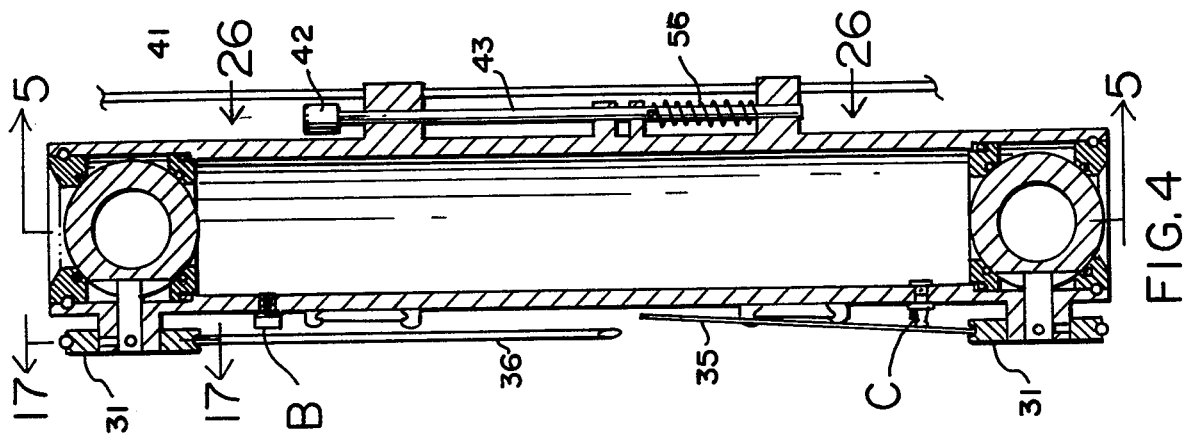
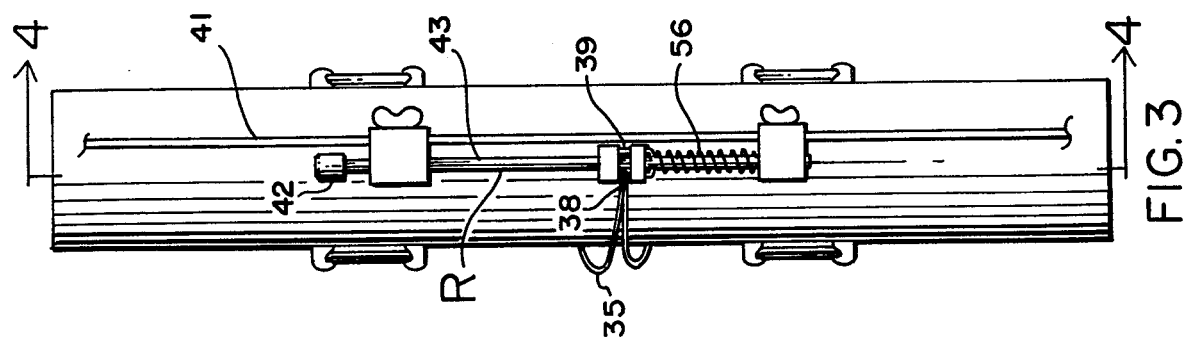
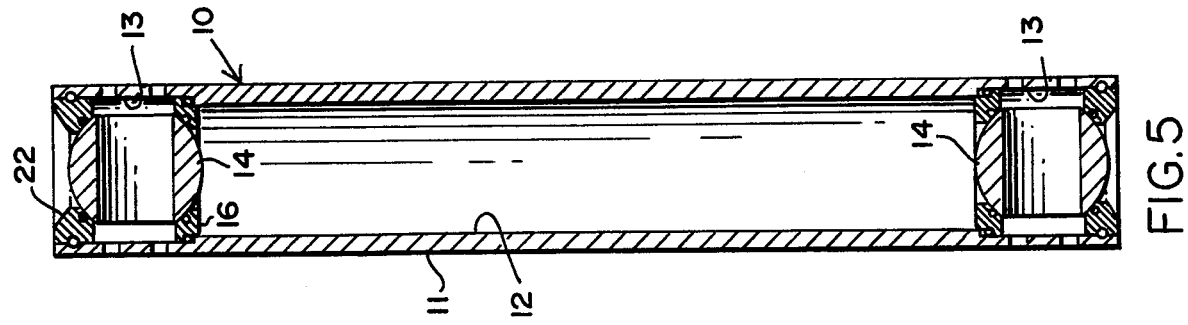
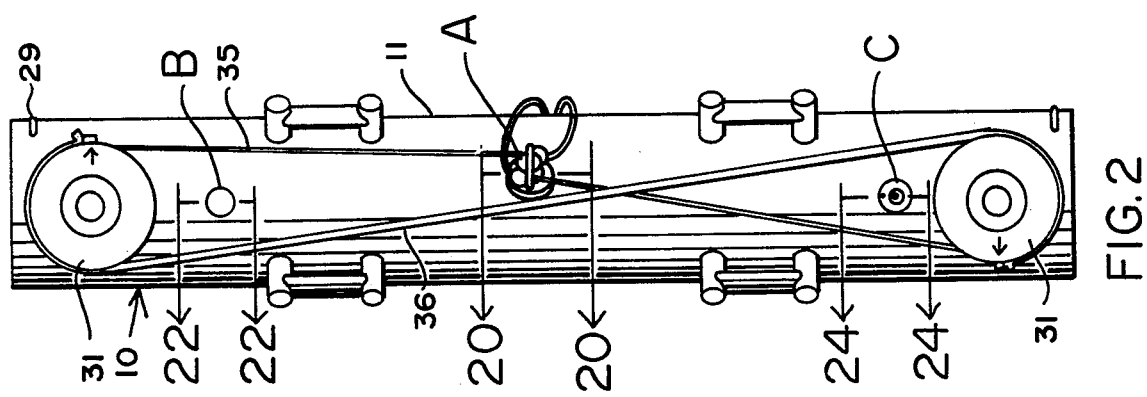

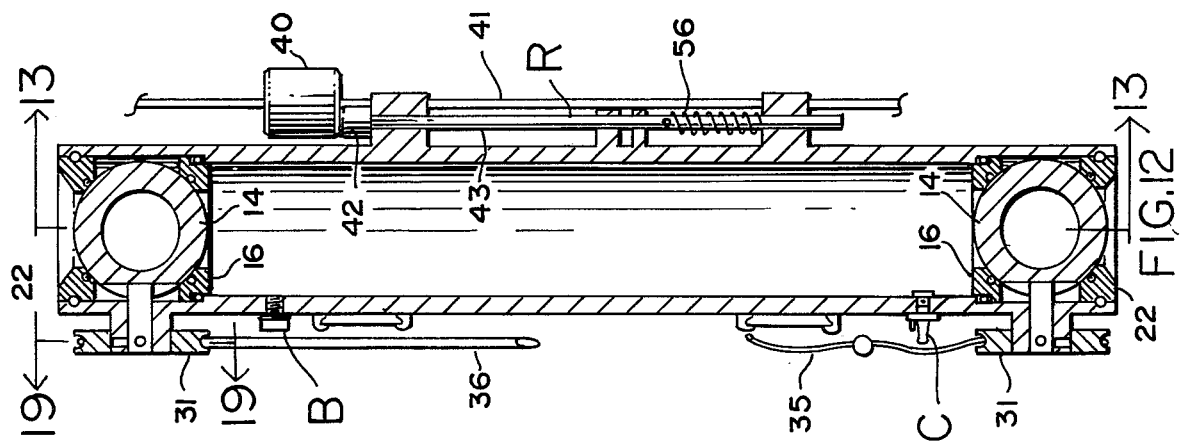
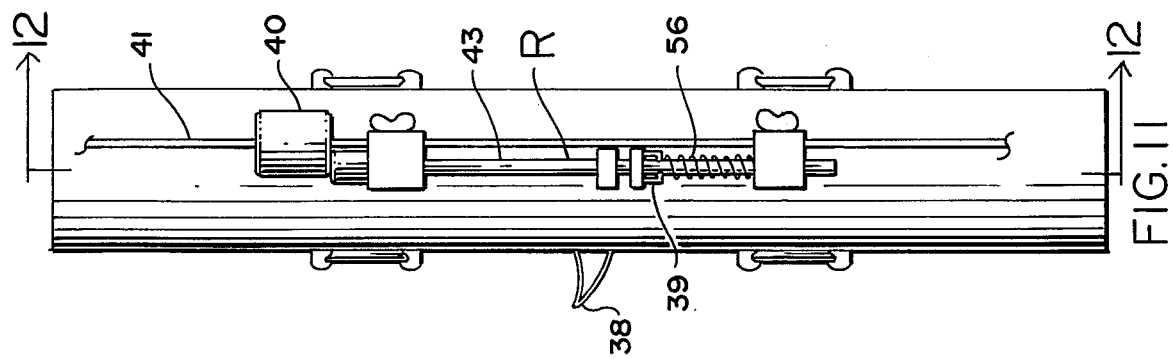
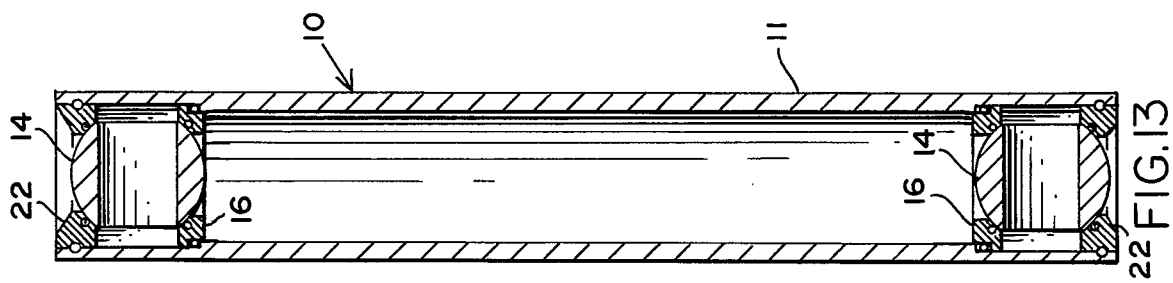
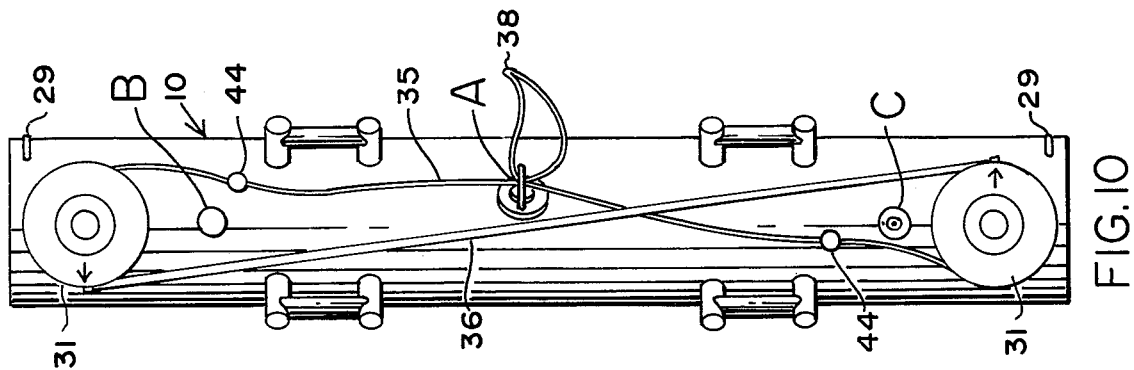

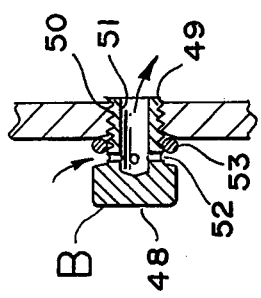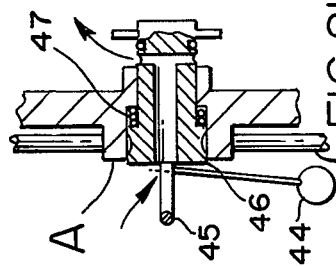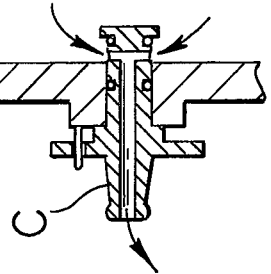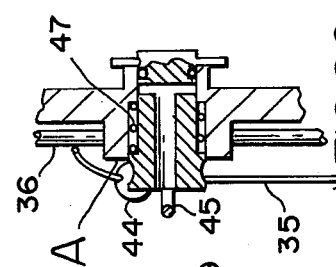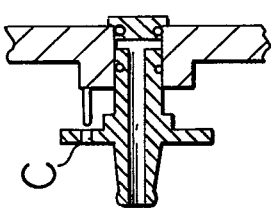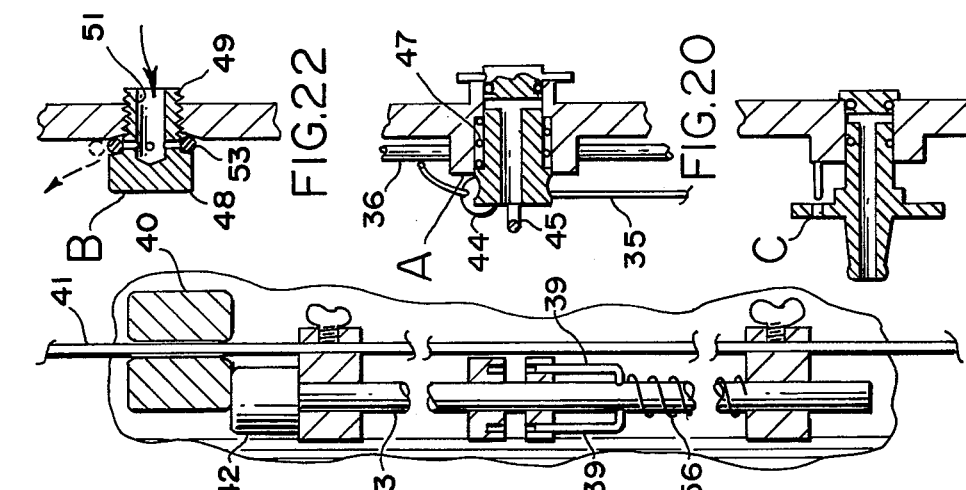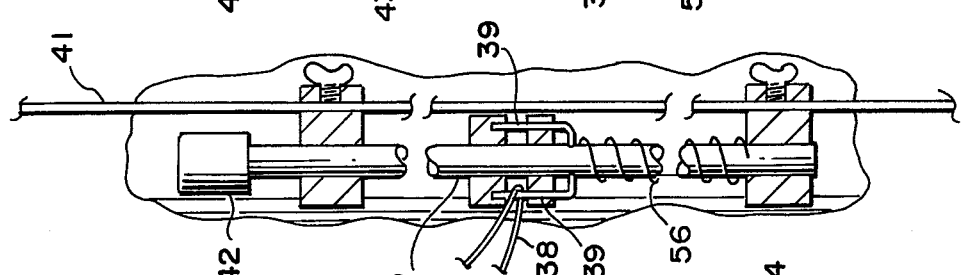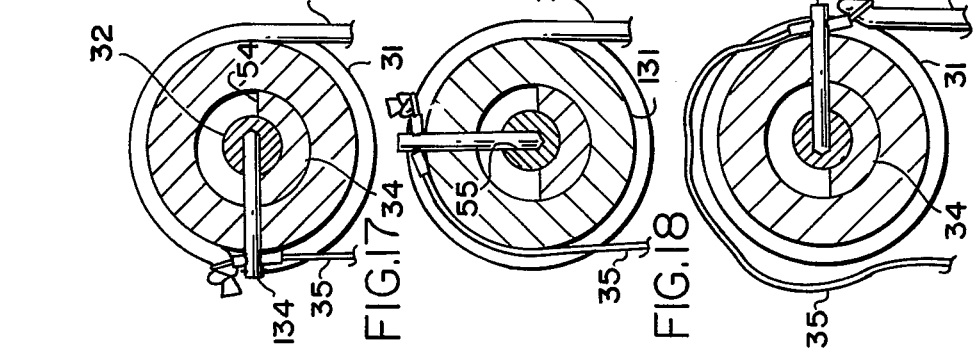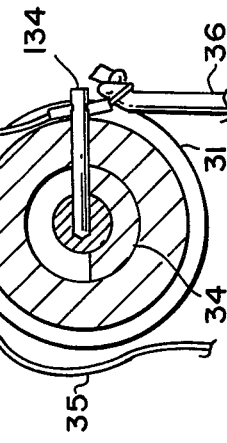

WATER SAMPLE COLLECTING DEVICE

CROSS REFERENCES TO RELATED APPLICATIONS

This application is a continuation-in-part of my application Ser. No. 691,905, filed on June 1, 1976, for Water Sampler Device issued on July 26, 1977 as U.S. Pat. No. 4,037,477.

BACKGROUND OF THE INVENTION

1. Field of the Invention

This invention relates to and is directed to water sample collecting devices.

2. Description of the Prior Art

The present invention is similar to and an improvement over the water sampler of my copending application Ser. No. 691,905 issued on July 26, 1977 as U.S. Pat. No. 4,037,477. The manner of securing the ball valves in position in a sealed position at each of the cylinders has been simplified, made more effective and less expensive in production costs. Also, the pressure relief valve has been improved while only a single lanyard is used instead of two in the operation of the ball valves. In all other respects the water sample collecting devices are identical in structure and operation.

SUMMARY OF THE INVENTION

Therefore, a principal object of the present invention is to provide a water sample collecting device having ball valves mounted at each end of a cylinder wherein the ball valves are capable of rotating readily from a first closed position to an open position, and then back to the closed position when the cylinder has become filled with a water sample.

Another object of the present invention is to provide a ball valve mounted at each end of a water collecting cylinder with a pair of valve lock rings engaging the ball valves and sealed by O-rings on either side whereby danger of malfunctioning of the ball valves is minimized yet the seal against leakage improved.

A further object of the present invention is to provide means for securing ball valves at the ends of a water sampler which is simple in construction and readily received in position when assemblying the device rather than the danger which presently exists of either securing the ball valves too tightly to permit the rotational movement of the ball valves or too loosely as to permit the leakage of water therealong.

A further object of the present invention is to provide a water sampler with ball valve rotational restraining means with a single lanyard rather than two lanyards as shown in the invention of the above indicated copending application.

A still further object of the present invention is to provide a water sample collecting device with an air vent pressure release utilizing an O-ring that seals the vent opening and expands to permit release of excess water pressure therethrough.

With these and other objects in view, the invention will be best understood from a consideration of the following detailed description taken in connection with the accompany drawings forming a part of this specification, with the understanding, however, that the invention is not confined to any strict conformity with the showing of the drawings but may be changed or modified so long as such changes or modifications mark no material departure from the salient features of the invention as expressed in the appended claims.

BRIEF DESCRIPTION OF THE DRAWINGS

In the drawings:

FIG. 1 is a perspective view of a water sampler constructed in accordance with my invention.

FIG. 2 is an elevational view of my water sampler ready to be launched to collect a sample of water with its ball valves in a closed position.

FIG. 3 is a similar view showing the obverse side of the water sampler.

FIG. 4 is a cross sectional view taken along the line 4—4 of FIG. 3.

FIG. 5 is a cross sectional view taken along the line 5—5 of FIG. 4.

FIG. 10 is an elevational view of the water sampler similar to FIGS. 2 and 6 showing the device after the ball valves have become closed to contain the desired sample of water therein.

FIG. 11 is a similar view showing the obverse side of the bottle.

FIG. 12 is a cross sectional view taken along the line 12—12 of FIG. 11.

FIG. 13 is a cross sectional view taken along the line 13—13 of FIG. 12.

FIG. 14 is an exploded view of one end of the water sampler showing the ball valve structure.

FIG. 17 is a cross sectional view taken along the line 17—17 of FIG. 4.

FIG. 18 is a cross sectional view taken along the line 18—18 of FIG. 8.

FIG. 19 is a cross sectional view taken along the line 19—19 of FIG. 12.

FIG. 20 is a fragmentary cross sectional view taken along the line 20—20 of FIG. 2.

FIG. 21 is a similar view taken along the line 21—21 of FIG. 6.

FIG. 22 is a fragmentary cross sectional view taken along the line 22—22 of FIG. 2.

FIG. 23 is a similar view showing the internal pressure relief valve actuated to release internal pressure.

FIG. 24 is a cross sectional view taken along the line 24—24 of FIG. 2 with the drain or stop cock in a closed position.

FIG. 25 is a similar view showing the drain or stop cock in an open position.

FIG. 26 is a fragmentary cross sectional view taken along the line 26—26 of FIG. 4.

FIG. 27 is a similar view showing the ball valve release mechanism in the released position.

DETAILED DESCRIPTION OF THE PREFERRED EMBODIMENT

Figure 8:
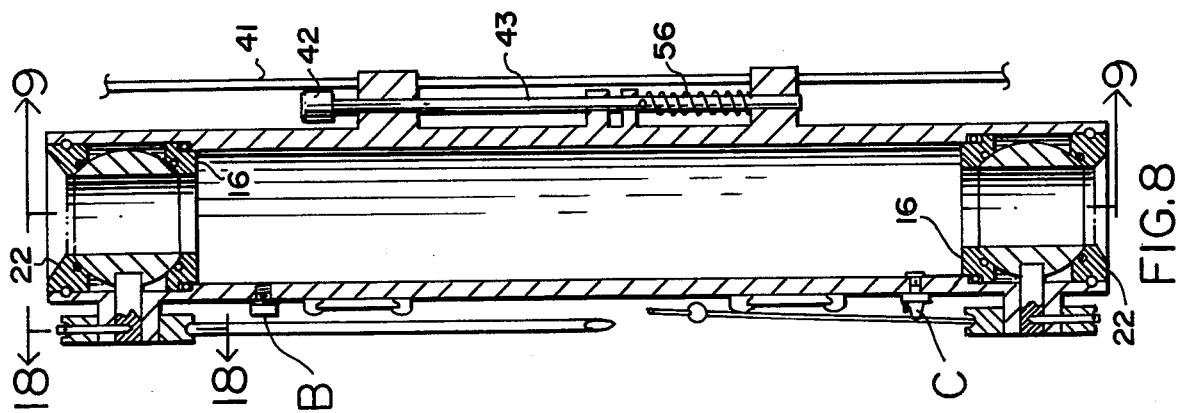
FIG. 8 is a cross sectional view taken along the line 8—8 of FIG. 7.
Figure 7:
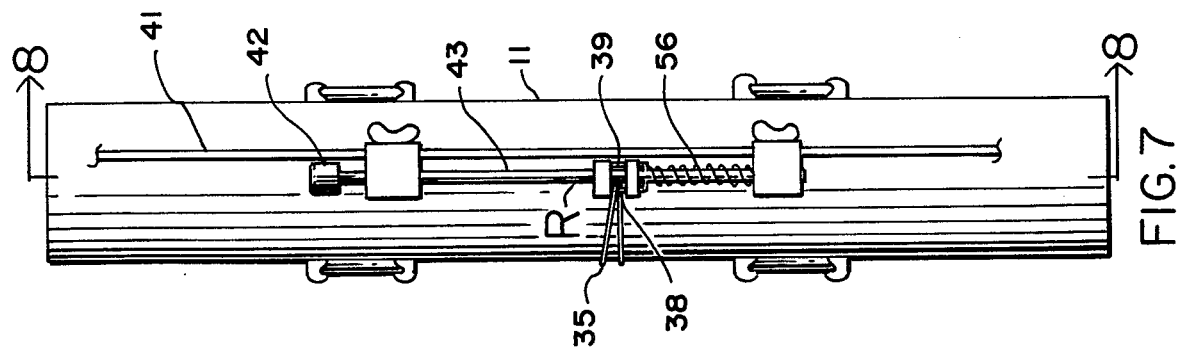
FIG. 7 is a similar view showing the obverse side of the bottle.
Figure 9:
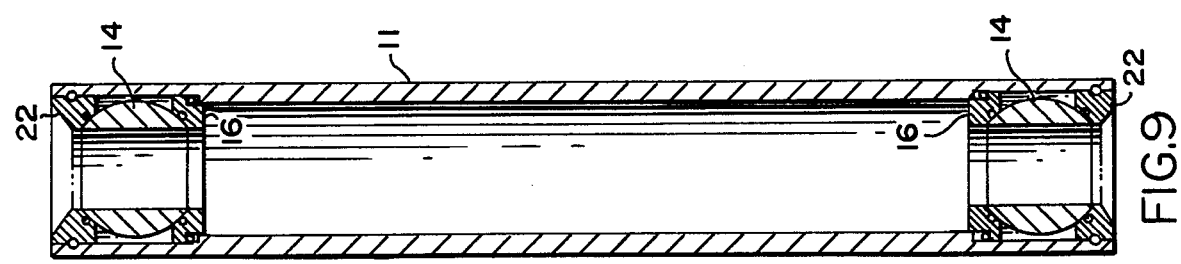
FIG. 9 is a cross sectional view taken along the line 9—9 of FIG. 8.

Referring to the drawings wherein like numerals are used to designate similar parts throughout the several views, the numeral 10 refers to my water sample collecting device that is identical in operation to the water sampler of my U.S. Pat. No. 4,037,477 No. 691,905, but different in the construction of the following indicated structure:

1. The ball valve retaining and sealing means.
2. The air vent and internal pressure release valve.
3. The use of a single lanyard rather than multiple lanyards for securing the ball valves in the initially closed positions and permitting the rotation of the ball valves in stages from the original closed position to an open position and then to the closed position to contain the sample of water therein.

The water sampler 10 consists of an elongated tubular member or bottle 11 having a chamber 12 at the ends of which are valve chambers 13. Within the valve chambers 13 are identical ball valves 14 rotatably mounted therein. Each of the valve chambers 13 is provided with a peripheral shoulder 15 on which an inner ring-shaped valve seat 16 is mounted. The valve seat 16 that has a centrally disposed opening 17 for the flow of water therethrough is provided with an outer peripheral shoulder 18 which bears on an O-ring 19 positioned between the shoulder 15 and 18 for sealing the juncture of the outer periphery of the valve seat 16 and inner surface of the bottle 11. An inner peripheral groove 20 extends about the opening 17 receives an O-ring 21 for sealing the valve seat 16 and ball valve 14 against the leakage of water therealong.

A fixed ring-shaped valve seat 22 is mounted at the free ends of the tubular member 11 engaging the ball valves 14 to maintain the ball valves 14 in a firm but rotatable condition within the chambers 13. The outer valve seats 22 are each provided with a centrally disposed opening 23 and an inner peripheral groove 24 adjacent the opening 23 for receiving a hollow O-ring 25 that engages the ball valve 14, for sealing same. The outer valve seat 22 is secured to the bottle 11 by peripheral matching grooves 26 and 27 formed on the inner surface of the bottle 11 and outer surface of the outer valve seat 22 respectively and a pliable locking rod 28 received therein, as shown and described in detail in my U.S. Pat. No. 3,986,635, for Closure Locking And Orienting Device. A bore 29 formed in the wall of the bottle 11 in alignment with the grooves 26 and 27 permits the threading of a pliable rod 28 into position in the matching grooves 26 and 27 to secure the valve seat 22. Openings 30 formed in the side walls of the bottle 11 prevent water from being trapped in the valve chamber 13 when the valves 14 are in an open position.

The O-ring 19 effects a watertight juncture between the valve seat 16 and cylinder 11 by its engagement of the outer periphery of the valve seat 16 on one side and the inner surface of the bottle 11 on the other side. After the bottle 11 is filled with water at the desired depth in the ocean, and the bottle 11 is being pulled upwardly with the valves 14 in a closed position, the higher pressure of the contained water will cause the valve seat 16 and ball valve 14 to slide outwardly for the valve seat 16 to bear more tightly against the ball valve 14 and the ball valve 14 to bear more tightly against the hollow O-ring 25. The O-ring 19 will roll within the groove formed between the shoulders 15 and 18 and not become pinched by the movement of the floating valve seat 16 so as to affect its watertight seal ability.

Figure 6:
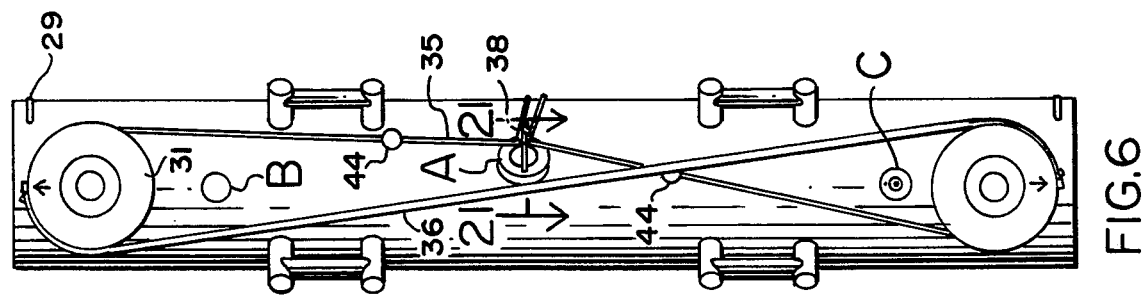
FIG. 6 is an elevational view similar to FIG. 2 showing the water sampler after being launched with the ball valves in an open position to permit water to flow through the bottle.
Figure 15:
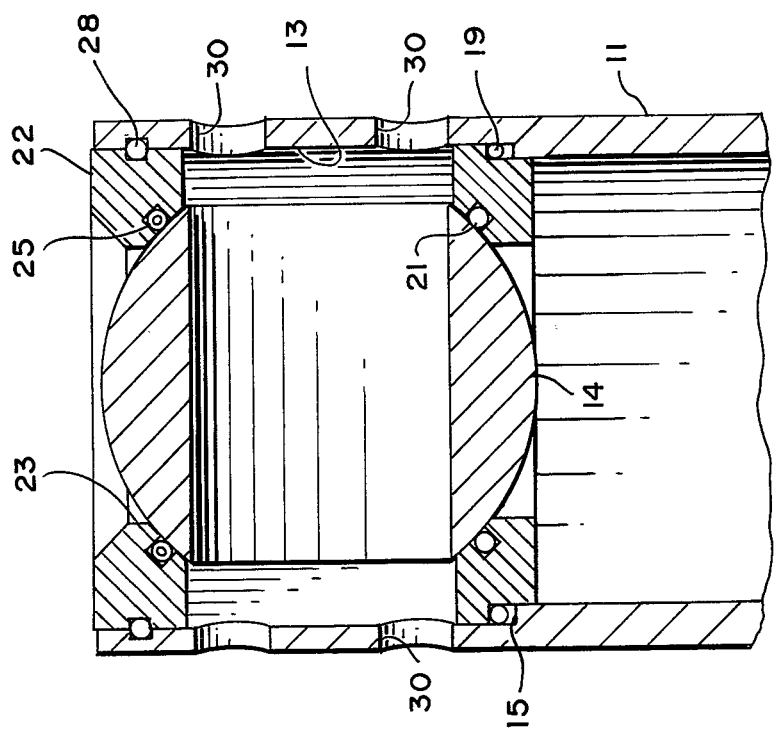
FIGS. 15 and 16 are fragmentary cross sectional views of one end of the water sampler showing the ball valve in a closed and open position respectively.
Figure 16:
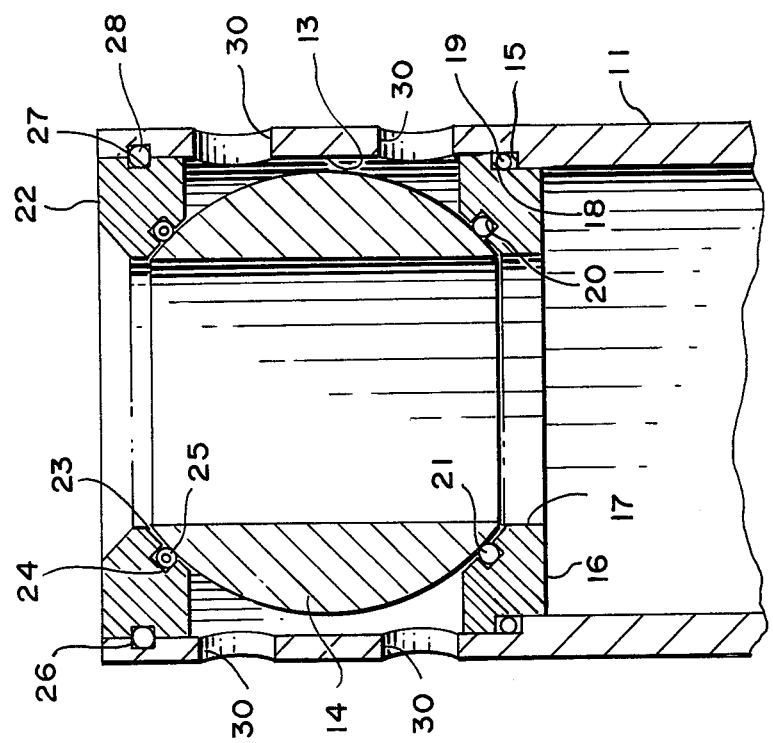

The ball valves 14 are each actuated by pulleys 31 secured to the end of a stub shaft 32 that extends through an opening 33 in a collar 34 mounted on the bottle 11. A pin 134 whose free end is secured to a lanyard 35 on one side and an elastic member 36 on the other side extends through a radial opening 37 in the pulley 31, a 180° slot 54 in the collar 34 and terminating in a bore 55 in the stub shaft 32. The latter is provided with a rectangular plug 60 that is received by a groove 61 on the ball valve 14 to rotate the valve 14. This structure permits the rotation of the pulleys 31 and simultaneous rotation of the valves 14 from a closed position as shown by FIGS. 5 and 17 through an arc of 90° to an open position as shown by FIGS. 6 and 18, and then a continued rotation of a further 90° arc of the valves 14 to a closed position as shown by FIGS. 10 and 19.

Extending between the pulleys 31 is the elongated elastic member 36 in an expanded condition having its ends wound about the groove 131 in the pulleys 31 with a yielding force tending to rotate the pulleys 31 but restrained therefrom by the lanyard 35. At approximately the mid-portion of the lanyard 35, a loop 38 is formed engaged by pins 39 of a release mechanism R shown by FIGS. 3, 26 and 27 which is explained in detail in my aforementioned application. When the bottle 11 has arrived at the desired depth at which a sample of water is to be obtained, a weighted messenger 40 is released to slide down the line 41 where it strikes the head 42 of a slide bar 43 which then slides downwardly against the spring force 56 to carry the pins 39 downwardly to release the loop 38 and permit the lanyard 38 to become free. As will be explained in detail hereinafter, the valves 14 which had been in the open position will now rotate to a closed position and entrap and contain the desired sample of water.

The valves 14 which are in the closed position when the sampler 10 is about to be launched are rotated to an open position by water pressure bearing against the pressure relief or venting valve A . This valve A is identical to that shown and described in my copending application. FIG. 20 shows the valve A in a closed position with a pair of balls 44 that are mounted on the lanyard 35 secured against movement by a metal guard 45 formed in a loop and secured to the valve body 46. A coil spring 47 maintains the valve body 46 in an extended and closed position. After the sampler 10 is launched, water pressure will cause the valve body 46 to slide inwardly to permit water to enter the bottle 11 as shown by FIGS. 6 and 21.

Also mounted on the bottle 11 is a pressure release valve B which releases the increased pressure of water in the bottle 11 as the bottle 11 is brought to the surface after having been filled with the sample at the desired depth. The valve B consists of a head portion 48 mounted on a threaded body portion 49 threaded in an opening 50 on the bottle 11. An axial bore 51 extends the length of the body portion 49 communicating with a plurality of radial bores 52 adjacent the head portion 48. Mounted about the body portion 49 is an O-ring 53 engaging the radial bores 52 so as to close off the O-rings 52 until the water pressure within the bottle 11 is greater than the pressure of the water surrounding the bottle 11. When this occurs as the filled bottle 11 is being brought up to the surface, the higher internal pressure will cause the O-ring to expand away from the radial openings 52 and the pressures between inside and outside of the bottle 11 become equalized. Also, when the conventional drain or stopcock C mounted on the bottle 11 is slid from its closed position as shown by FIG. 24 to its open position as shown by FIG. 25 to evacuate the sample of water from the bottle 11, the release valve B can be threaded outwardly to permit air to enter the bottle 11 as shown by FIG. 23. The stopcock C is conventional in structure and explained in detail in my copending application.

The operation of my sampler device 10 is similar to that shown by my U.S. Pat. No. 4,037,477 in that the valves 14 are in a closed position at launching; they rotate 90° to an open position after being launched when the water pressure causes the valve A to be actuated, releasing the balls 44 on the lanyard 35. The loop 38 secured to the balls 44 become tightened on the prong 38 as shown by FIGS. 10, 18 and 26 to permit only a 90° rotation of the valves 14 to the open position. Upon the sampler 10 arriving at its desired depth and the messenger 40 striking the slide rod head 42, the loop 38 is released and the elastic member 36 forcing the continued rotation of the pulleys 31 and valves 14 to the closed position as shown by FIGS. 10, 19 and 27.

What I claim as new and desire to secure by Letters Patent is:

1. In a water sample collecting device having a tubular member with open end portions, an internal peripheral shoulder mounted about said tubular member in said end portions, valve means mounted at said end portions, said valve means comprising inner valve seat means having an external peripheral shoulder, said inner valve seat means being responsive to the pressure of the water sample collected at a predetermined depth and slidably positioned at the inner end of said end portions in proximity of said internal peripheral shoulder, a spherical valve seated on said valve seat means, a substantially centrally disposed opening in said valve seat means, a peripheral groove formed on said valve seat means about said opening, first sealing means mounted in said peripheral groove engaging said spherical valve and sealing the juncture therebetween, second sealing means mounted about said valve seat means and positioned between said internal and external shoulders, outer valve seat means having a substantially centrally disposed opening, said outer valve seat means being mounted at the outer end of said end portions, a second peripheral groove formed on said outer valve seat means about said last named opening, third sealing means mounted in said second peripheral groove engaging said spherical valve and means securing said outer valve seat means to said tubular member.

2. The structure as recited by claim 1 wherein said securing means comprising a further external peripheral groove formed about said outer valve seat means, an internal groove formed on said tubular member in substantially coplanar relation with said further external groove, an opening in said tubular member in alignment with said further groove and a pliable rod extending through said opening and said aligned further external peripheral and internal grooves to span the junction thereof whereby said outer valve seat means are secured in position in said end portions.

3. The structure as recited by claim 2 wherein all of said sealing means consist of O-rings.

4. The structure as recited by claim 3 wherein said third sealing means consist of hollow O-rings.

5. The structure as recited by claim 4 wherein said spherical valves having an axially disposed opening in substantial alignment with said inner and outer valve seat means and a plurality of openings in said tubular member at said end portions to prevent trapping water in said portions when said spherical valves are in an open position.

6. The structure as recited by claim 1 taken in combination with an internal pressure release valve comprising a head portion and body portion threadedly mounted on said tubular member, an axially disposed passageway extending through said body portion and terminating adjacent said head portion, a plurality of radially disposed bores mounted on said body portion adjacent said head portion communicating with said passageway and an O-ring mounted on said body portion and engaging said bores whereby upon the pressure being higher within said tubular member than the outside thereof, said O-ring will become expanded to permit the escape of fluid through said bores until said pressures become substantially equalized.

7. The structure as recited by claim 5 taken in combination with an internal pressure release valve comprising a head portion and body portion threadedly mounted on said tubular member, an axially disposed passageway extending through said body portion and terminating adjacent said head portion, a plurality of radially disposed bores mounted on said body portion adjacent said head portion communicating with said passageway and an O-ring mounted on said body portion and engaging said bores whereby upon the pressure being higher within said tubular member than the outside thereof, said O-ring will become expanded to permit the escape of fluid through said bores until said pressures become substantially equalized.

* * * * *